(12) United States Patent
Gantner et al.

(10) Patent No.: US 8,101,042 B2
(45) Date of Patent: Jan. 24, 2012

(54) METHOD FOR ADHERING SILICONE GELS TO PLASTICS

(75) Inventors: David Clayton Gantner, Midland, MI (US); Gary Lee Loubert, Saginaw, MI (US); Gerald Kenneth Schalau, II, Freeland, MI (US); Xavier Jean-Paul Thomas, Foix (FR)

(73) Assignee: Dow Corning Corporation, Midland, MI (US)

( * ) Notice: Subject to any disclaimer, the term of this patent is extended or adjusted under 35 U.S.C. 154(b) by 1045 days.

(21) Appl. No.: 10/577,032

(22) PCT Filed: Sep. 30, 2004

(86) PCT No.: PCT/US2004/032568
§ 371 (c)(1), (2), (4) Date: Apr. 20, 2006

(87) PCT Pub. No.: WO2005/051442
PCT Pub. Date: Jun. 9, 2005

(65) Prior Publication Data
US 2007/0042108 A1    Feb. 22, 2007

Related U.S. Application Data

(60) Provisional application No. 60/519,702, filed on Nov. 13, 2003.

(51) Int. Cl.
*C09J 5/02* (2006.01)
*B32B 37/15* (2006.01)
*B32B 37/26* (2006.01)
*B32B 38/10* (2006.01)
*C09J 5/04* (2006.01)
*C09J 5/10* (2006.01)
*B29C 65/48* (2006.01)

(52) U.S. Cl. .................. 156/308.6; 156/249; 156/284; 156/289

(58) Field of Classification Search ............... 156/284, 156/308.6, 249, 289
See application file for complete search history.

(56) References Cited

U.S. PATENT DOCUMENTS

| 3,020,260 | A | 2/1962 | Nelson | |
|---|---|---|---|---|
| 6,129,854 | A * | 10/2000 | Ramsey et al. | 216/18 |
| 6,475,329 | B1 | 11/2002 | Johnson et al. | |
| 6,512,072 | B1 * | 1/2003 | Gantner et al. | 528/34 |
| 6,846,508 | B1 | 1/2005 | Colas et al. | |
| 7,914,645 | B2 * | 3/2011 | Schalau et al. | 156/329 |
| 2006/0083776 | A1 * | 4/2006 | Bott et al. | 424/445 |
| 2007/0202245 | A1 * | 8/2007 | Gantner et al. | 427/2.1 |

FOREIGN PATENT DOCUMENTS

| EP | 0 300 620 | 6/1988 |
|---|---|---|
| EP | 0 261 167 | 1/1992 |
| EP | 0 322 118 | 6/1992 |
| EP | 0 399 520 | 11/1996 |
| EP | 0 995 347 | 2/2002 |
| FR | EP0955347 A2 * | 11/1999 |
| GB | 849885 | 6/1959 |
| GB | 945580 | 2/1962 |
| GB | 2192142 | 7/1986 |
| JP | 03-106977 | 5/1991 |
| JP | 03106977 A * | 5/1991 |
| JP | 3024978 | 1/2000 |
| WO | WO 95/22997 | 8/1995 |
| WO | WO 96/09076 | 3/1996 |
| WO | WO 99/03424 | 1/1999 |

OTHER PUBLICATIONS

English Abstract of JP 03-106977. May 7, 1991; Miyoshi et al.*

* cited by examiner

*Primary Examiner* — Sonya Mazumdar
(74) *Attorney, Agent, or Firm* — Timothy J. Troy

(57) ABSTRACT

A method for increasing the adherence of a silicone gel to a substrate using a primer material. The method is particularly useful for adhering a medical prosthesis to a human or animal body.

24 Claims, No Drawings

METHOD FOR ADHERING SILICONE GELS TO PLASTICS

CROSS REFERENCE TO RELATED APPLICATIONS

This application is a U.S. national stage filing under 35 U.S.C. §371 of PCT Application No. PCT/US04/032568 filed on 30 Sep. 2004, currently pending, which claims the benefit of U.S. Provisional Patent Application No. 60/519702 filed 13 Nov. 2003 under 35 U.S.C. §119 (e). PCT Application No. PCT/US04/032568 and U.S. Provisional Patent Application No. 60/519702 are hereby incorporated by reference.

The present invention relates to a method for adhering a silicone gel to a substrate in which a primer material is used to increase the adhesion of the silicone gel to the substrate. This method is especially useful for adhering silicone gels to medical prosthesis so that the silicone gel can adhere the prosthesis to a human or animal body.

Pressure sensitive adhesives (PSAs), including silicone PSAs, and tapes containing such adhesives are known in the art and many are commercially available. Typically, silicone PSAs comprise condensed blends of silicone fluids and silicone resins. Typically, such silicone PSAs are applied as thin coatings between substrates to be adhered together.

It is likewise known in the art to use silicone PSAs in medical applications. For instance, it is known to use silicone PSAs to adhere transdermal drug delivery devices and medical prosthesis to patients.

Silicone PSAs, however, can have a number of properties that limit their use in medical applications. For instance, the adhesive strength of silicone PSAs is often so great that a patient's skin or the object to be adhered can be damaged on removal of the PSA. Additionally, silicone PSAs often exhibit cold flow properties at skin temperature. As such, the resultant inflexible layers of PSA can be very uncomfortable on the patient's body. Finally, silicone PSAs often delaminate from the carrier leaving a coating of the PSA on the skin and/or the object to be adhered. Not only is this a cosmetic problem, but it also limits the ability to reuse the adhesive.

Silicone gels are also known in the art and described, for instance, in WO95/22997, WO96/09076 and EP300,620. These gels have been used, for example, as dielectrics, vibration dampers and in medical therapy for cutaneous scars or injuries (e.g., abrasions, surgical areas or burns). In this latter use, the silicone gel is in the form of a sheet with one tacky surface for adherence to the patient's skin and one non-tacky surface to inhibit undesirable adhesion to the gel (e.g., the patient's clothing). An adhesive gel was likewise disclosed in EP995,347 but the present primers were not described therein.

When silicone gels are joined with certain substrates such as plastics, however, the adhesive strength between the silicone gel and the plastic is often so weak that it delaminates. As such, when the silicone gel is used as an adhesive to adhere a prosthesis to a human or animal body, the gel often delaminates from the prosthesis before the gel delaminates from the human or animal body to which it is applied.

To increase adhesion of silicones to plastics, the art has suggested treating the substrate such as a plastic surface with means such as corona, flame, and plasma. While such treatments are beneficial, they are difficult to implement on a continuous coating line. Moreover, the treatments must be precisely controlled to prevent damage to the substrate (e.g., heat damage) or inhibit the cure of the silicone material.

We have now discovered that by putting a primer material between the silicone gel and the substrate the adhesive strength of the gel to the substrate is increased.

Accordingly, in one of its aspects the present invention provides a method for adhering a silicone gel to a substrate. The method comprises first forming a silicone gel. A surface of the silicone gel is then treated with a primer material. -The treated surface of the silicone gel is then joined to a surface of a substrate to which it is to be adhered.

In an alternative embodiment a silicone gel is formed. A surface of a substrate to which the gel is to be adhered is then treated with a primer material. The silicone gel is then joined with the treated surface of the substrate to which it is to be adhered.

In another of its aspects, the present invention provides a composition comprising a substrate. On the surface of the substrate is a primer material. On the primer material is a layer of a silicone gel.

In yet another of its aspects, the present invention provides a method for adhering a prosthesis to a human or an animal body. The method comprises forming a layer of a silicone gel on a releasable substrate. A surface of the silicone gel or of the prosthesis is treated with a titanate material. The surface of the silicone gel is then joined with the prosthesis. The silicone gel having the prosthesis applied thereto is removed from the releasable substrate. The silicone gel having the prosthesis applied thereto is applied to a human or animal body.

This process can be used to adhere the silicone gel to substrates such as plastics, natural macromolecular materials (e.g. collagen, wood, cork, leather), metals, glass, ceramics or composites.

The adhesion and physical properties of the gels used in the present invention can be tailored to specific end uses by modifying the primer material and/or the gels. Moreover, because of the ease in removability and because the gel generally maintains its tack after removal, the gels of the invention can be reused. In addition, the reusability allows for easy and comfortable repositioning of medical prosthesis. Finally, silicone gels lack cold flow and, as such, are sufficiently soft to allow comfortable use by a human or animal.

DESCRIPTION

In its most generic form, the method of the present invention comprises using a primer material to increase the adherence of a silicone gel to a substrate. The substrate can comprise plastics, natural macromolecular materials (e.g. collagen, wood, cork, leather), metals, glass, ceramics or composites.

The substrates used herein can comprise plastics or resins known in the art. Representative examples include polyolefins including polyethylenes (low density polyethylenes, high density polyethylenes and the like), polypropylenes, polybutylenes, polymethylpentenes, polyethylene-vinyl acetate (EVA) and their copolymers, polyvinyls, polyvinyl acetates, polyvinyl alcohol, polyvinylbutyral, polyvinyl formal, polyurehianes and polyurethane-ureas, polyvinyl chloride derivatives (polyvinyl chloride, polyvinylene chloride, copolyvinylchloride-propylene), polystyrenes and their copolymers (copolystyrene-butadiene, polystyrene acrylonitrile, polyacrylonitrile-butadiene-styrene), polyacrylic and polyacrylates derivatives (polymethyl methacrylate, ethylene/butyl acrylate copolymer, ethylene/methyl acrylate copolymer, ethylene/methacrylic acid copolymer), polyacrylonitrile, polyesters (including PETE, polyethylene terephtalate, polybutylene terephtalate, polyvinylacetate, polylactic-glycolic derivatives), cellulosic films (nitrocellulose, ethylcellulose, cellulose acetate, cellulose acetate butyrate, cellulose propionate), polyimides, polyamides (nylon), epoxy and phenolic plastics, silicone elastomers, polycarbonates, phenoplastes, fluorinated polymers (polytetrafluoroethylene, polyvinylidene fluoride), polyoxymethylenes, polyphenylene oxides, polysulfones (PSU, PESU, PPSU), polyphenyl sulfide, silicones and polysaccharide based materials.

The substrates used in the present invention can be in nearly any configuration. For example, it can be in the form of a prosthesis or a continuous or perforated plastic film, a nonwoven film, a knitted fabric, a fiber network, a foam, a metal, a glass or ceramic material. It is often preferred herein to have the substrate in the form of a prosthesis. Examples include breast prosthesis, catheters, cannulas, drainage bags, uridomes, incontinence devices, hygiene napkins, pouches, false hairpieces (e.g., toupees), tubes, ostomy and related devices, surgery drapes, facial masks, gloves, and the like.

The silicone gel layer used in the present invention should be chosen to have the properties desired for the end application. If used for adhering prosthesis to patients, the gels should have sufficient tack to adhere to the body of the patient. The silicone gel should also be soft so that it is comfortable for the user and non-friable so that it is durable for its intended use.

The gels used in the present invention are generally formed from linear or branched silicones having reactive groups thereon, as is known in the art. Such reactive groups undergo a cross-linking reaction during curing. Examples of cross-linking reactions include the hydrosilylation reaction in which a silicone having an Si—H reactive group reacts with a silicone having an aliphatically unsaturated reactive group in the presence of a platinum or rhodium catalyst. Alternatively, the reaction can involve the reaction of a silicone having an Si—OH reactive group with a silicone or a chain extender (e.g., a silane) having an alkoxy reactive group in the presence of a metal catalyst. In yet another alternative embodiment, a silicone having an Si-OH containing polymer is mixed with an alkoxysilane in the presence of a titanate catalyst. Other known cure mechanisms such as that described in U.S. Pat. No. 6,512,072, which is incorporated herein by reference, are also effective herein.

The preferred gels herein are obtained by reacting an alkenyl-substituted polydiorganosiloxane, preferably a polydimethylsiloxane having silicon-bonded vinyl, allyl or hexenyl groups, an organosiloxane containing silicon-bonded hydrogen atoms and a catalyst for the reaction of the SiH groups with the Si-alkenyl groups, such as a platinum metal or compounds or complexes thereof. Such compositions cure at normal ambient temperatures, but curing can be expedited by exposure to elevated temperatures, e.g., from about 40° C. to about 120° C.

Preferred Si—H and Si-alkenyl siloxanes to be used in the above reaction have viscosities in the range of 5 to 60,000 mm$^2$/second. The preferred ratio of (I as SiH)/(Alkenyl as Si-Alkenyl) is generally in the range of 0.1:1 to 10:1.

If desired, other components can be included in the gels of the present invention including, but not limited to, fillers, pigments, low temperature cure inhibitors, additives for improving adhesion, pharmaceutical agents, cosmetic agents, resins, fluids or other materials conventionally used in gels.

Suitable gels and gel forming compositions are described in, for example, G.B. Patents 849,885; 945,580 and 2,192, 142, U.S. Pat. No. 3,020,260, and EP 399,520; EP261,167; EP300,620 and EP322,118, which are incorporated herein by reference.

The consistency, strength and tackiness of the gel is determined by a number of factors including the ratio of reactive groups in the materials, the viscosity of the polymers, and the like. One skilled in the art would know how to adjust this ratio to obtain a product with the properties desired for a given use.

As measured by the Cone Penetration Test method based on ASTM D-217-88, gels often have a penetration of 50 mm to 300 mm with a cone category 1806-1 weighted 62.5 g.

Generally, the gels have a coating weight in the range of about 100 to 4500 g/m$^2$ with alternative densities in the range of about 150 to 1200 g/m$^2$. Such gels would generally have thicknesses in the range of about 0.2 to about 5 mm, alternatively of 0.2 to 1.5 mm.

The adhesive strength of the silicone gels should be sufficient to maintain adhesion for the desired use. If the gels are used to adhere a prosthesis to a patient, the adhesive strength of the gel should be sufficient to ensure that the prosthesis remains attached to the patient and yet not so strong that excessive numbers of skin cells are removed when the gel is removed. When measured with a Probe Tack Tester, the tack is generally between 50 g and 500 g, alternatively 150 g to 350 g. The adhesive property can also be measured using a Texture Analyzer (1/2 inch diameter cylinder Derlin probe, 100 gf applied for 5 seconds and 10 mm/s separation speed) the tack is generally between 50 gf to 500 gf.

The silicone gels should also be sufficiently soft and flexible to ensure comfort to the user. However, since softness also generally results in weaker gels, these two factors should be considered in selection and formulation of the gel.

If desired, the surfaces of the gels to be adhered to the patient can be covered or protected with a release liner prior to use. The adhesive strength between the silicone gel and such release liner is obviously less than that between the gel and the substrate material such that the release liner can be peeled off of the silicone gel revealing the underlying tacky gel. Suitable release liner materials are known in the art and can include, for instance, a plastic or multi-ply material such as a silicone, a fluorinated silicone, a fluorine polymer, polyethylene, ethylvinyl acetate polymer, a PVC or the like. Additionally, the release liner could be made from a wide variety of materials (e.g., paper) coated with a suitable release coating. Finally, the surface of the release coating can be smooth, embossed or in any other desirable form.

As noted above, silicone gels often do not adhere well to certain substrates such as plastics and, thus, delaminate. As such, the applicants herein have discovered that by priming either the surface of the silicone gel or the substrate with a primer, the adhesive strength of the silicone gel to the substrate is increased.

Suitable primers include titanate materials such as organic titanates commercialized by Dupont® under Tradename Tyzor®; organic zirconate; hydrogen functional siloxanes such as dimethyl, methylhydrogen siloxane, trimethylsiloxy-terminated, methylhydrogen siloxane, trimethylsiloxy-terminated, dimethyl siloxane, hydrogen-terminated, and methylhydrogen cyclosiloxanes; and platinum derivatives such as 1,3-diethenyl-1,1,3,3-tetramethyldisiloxane complexes (platinum).

Typically, the primers are applied as pure material or, if desired, they can be diluted (for example 0.1% to 50% by weight primer) in diluents such as volatile silicones, hydrocarbons (e.g. heptane), alcohols (e.g. isopropyl alcohol).

The primers can be applied to the surface by known means such as spraying, brushing, coating with a blade, roll transfer coating, wiping, dipping and the like.

The primer composition may contain materials other than those included above. For example, the primer may contain other adhesives such as silicone adhesives, other adhesion enhancers such as, for example silanes (e.g. trimethoxysilane), stabilizers, light or UV absorbers, pigments, dyes, inks, barrier materials to moisture and gas permeation, preservatives, and pharmaceutical or cosmetic agents which can either remain at the interface or release through the silicone gel, and the like.

The composition of the present invention can be made by any desirable technique. One example comprises preforming the gel (e.g., as a sheet) by known procedures e.g. by molding, calendering, extruding, spraying, brushing, applying by hand, coating or casting on, for example, a releasable substrate. A surface of the gel or the substrate can then be treated with the primer and the treated gel/substrate brought together with the substrate. For example, the gel may be preformed (e.g., as a sheet) by casting and curing the gel-forming composition on a suitable substrate. A surface of the gel can then be treated with the primer and the treated surface of the gel brought together with the substrate. Alternatively, the gel may be preformed (e.g., as a sheet) by casting and curing the gel-forming composition on a suitable substrate. A surface of the substrate can then be treated with the primer and the treated surface of the substrate brought together with the gel.

In the above processes, the gel forming composition may be applied by techniques such as spraying, coating, bar coating, etc. If desired, the gel forming composition can be used as a dispersion or solution in a volatile solvent such as an organic solvent, a low molecular weight silicone or other suitable solvent and, thereafter, the solvent can be evaporated.

In the above process, the gel forming composition may be applied as a continuous layer, a perforated layer, or a discontinuous layer forming various designs such as lines, dots, circles etc. Alternatively, the gel could be formed into any desirable configuration.

The substrate onto which the gel is applied in the above processes can be any surface that will impart the desired configuration to the compositions. Thus, it may be a continuous belt onto which the gel forming composition is spread. Depending on the consistency of the compositions, the substrate may have barriers at its edges to restrict the flow of the compositions until cure takes place. Preferably, the substrate is a releaseable substrate to allow the gel to be easily removed and used.

If desired, the substrate can be a preformed blister package made of any of the conventional blister packaging materials including, for example, polyvinyl chloride, polypropylene, polyethylene, polyester, paper or composites with or without suitable release coatings.

Other approaches that can be used include, for example, coating the surface of the substrate with the primer followed by application of the silicone gel precursor to the coated substrate and curing such precursor into the gel. Alternatively, the primer could be blended with the silicone gel precursor, the gel precursor deposited on the substrate followed by curing the gel precursor.

The gel composition formed above can be any size and shape desired based on the final use. For instance, it can be circular, square or rectangular and it can vary from a few square centimeters to in excess of several hundred square cm.

The compositions of the present invention are useful in applications where the adhesion provided by a silicone gel is useful. This can include, for example, adherence that requires shock absorbance such as in electrical components or in transportation devices and in application that require non-rigid adherence such as in construction. The silicone gel adhesives of this invention are, however, particularly adapted for adhering medical prosthesis on patients. Examples of such prosthesis include devices such as breast prosthesis, catheters, cannulas, drainage bags, uridomes, incontinence devices, hygiene napkins, pouches, false hairpieces (e.g., toupees), tubes, ostomy and related devices, surgery drapes, facial masks, gloves, other medical devices and the like.

If a prosthesis is to be adhered to a human or animal, the process can comprise forming a layer of a silicone gel on a releasable substrate. A surface of the silicone gel is treated with a titanate material. The treated surface of the silicone gel is then applied to a prosthesis. Finally, the silicone gel having the prosthesis applied thereto is removed from the releasable substrate and applied to a human or animal body.

Other applications include the manufacturing of silicone adhesive tapes (e.g. polyurethane nonwoven/fabric with silicone gel on it), gel sheeting (e.g. polyurethane film with gel on it), wound dressings (e.g. polyurethane film or polyurethane foam with gel on it), bandages, adhesive strips, surgery drapes (e.g., polyethylene with gel on it), topical or transdermal patches, fragrance/cosmetics patches and the like.

The following Examples illustrate the invention. Unless otherwise indicated, all percentages are by weight and all viscosities are at 25° C.

EXAMPLES 1-17

The compositions used in the Examples were made as detailed below. The gel forming composition was made by mixing equal parts of a Part (A) comprising 99.75 wt. % vinyl terminated polydimethylsiloxane and 0.25 wt. % platinum complex catalyst and Part (B) comprising 85 wt. % vinyl terminated polydimethylsiloxane and 15 wt. % Si—H functional polydimethylsiloxane.

The primers used in the Examples were as follows:
S1. 5% tetra-n-butyl titanate (TNBT)+5% trimethoxymethylsilane (TMMS) in 2-propanol (IPA)
S2. 10% INBT+10% TMMS in IPA
S3. 5% TNBT+5% TMMS in hexamethyldisiloxane (HMDS)
S4. 10% TNBT+10% TMMS in HMDS
S5. 5% TNBT in IPA
S6. 10% TNBT in IPA
S7. 5% TNBT in HMDS
S8. 10% TNBT in HMDS
S9. Pure TNBT A. The compositions were made as follows:
C1—Spray 1 g of S1 on a 25 cm×12.5 cm piece of polyurethane film. S1 was allowed to dry for 5 minutes at room temperature. Coat 250 g/m$^2$ of the gel precursor on Mylar®.
The polyurethane film coated with S1 was then gently laminated without pressure with the gel precursor coated on the Mylar®. The composition was then cured for 6 min at 140° C.
C2—Spray 1 g of S2 on a 25 cm×12.5 cm piece of polyurethane film. S2 was allowed to dry for 5 minutes at room temperature. Coat 250 g/m$^2$ of the gel precursor on Mylar®. The polyurethane film coated with S1 was then gently laminated without pressure with the gel precursor coated on the Mylar®. The composition was then cured for 6 min at 140° C.
C3—Spray 1 g of S5 on a 25 cm×12.5 cm piece of polyurethane film. S1 was allowed to dry for 5 minutes at room temperature. Coat 250 g/m$^2$ of the gel precursor on Mylar®. The polyurethane film coated with S1 was then gently laminated without pressure with the gel precursor coated on the Mylar®. The composition was then cured for 6 min at 140° C.
C4—Spray 1 g of S6 on a 25 cm×12.5 cm piece of polyurethane film. S1 was allowed to dry for 5 minutes at room temperature. Coat 250 g/m² of the gel precursor on Mylar®. The polyurethane film coated with S1 was then gently laminated without pressure with the gel precursor coated on the Mylar). The composition was then cured for 6 min at 140° C.

C5—Coat 250 g/m² gel precursor on an embossed polyethylene film. The gel precursor was cured for 20 min at 80° C. 1 g of S1 was sprayed on a 25 cm×12.5 cm piece of polyurethane film. S1 was allowed to dry 5 for minutes at room temperature. The gel on the embossed polyethylene film was laminated with the primed polyurethane film and cured for 3 minutes at 80° C.

C6—Coat 250 g/m² gel precursor on an embossed polyethylene film. The gel precursor was cured for 20 min at 80° C. 1 g of S2 was sprayed on a 25 cm×12.5 cm piece of polyurethane film. S1 was allowed to dry 5 for minutes at room temperature. The gel on the embossed polyethylene film was laminated with the primed polyurethane film and cured for 3 minutes at 80° C.

C7—Coat 250 g/m² gel precursor on an embossed polyethylene film. The gel precursor was cured for 20 min at 80° C. 1 g of S3 was sprayed on a 25 cm×12.5 cm piece of polyurethane film. S1 was allowed to dry 5 for minutes at room temperature. The gel on the embossed polyethylene film was laminated with the primed polyurethane film and cured for 3 minutes at 80° C.

C8—Coat 250 g/m² gel precursor on an embossed polyethylene film. The gel precursor was cured for 20 min at 80° C. 1 g of S4 was sprayed on a 25 cm×12.5 cm piece of polyurethane film. S1 was allowed to dry 5 for minutes at room temperature. The gel on the embossed polyethylene film was laminated with the primed polyurethane film and cured for 3 minutes at 80° C.

C9—Coat 250 g/m² gel precursor on an embossed polyethylene film. The gel precursor was cured for 20 min at 80° C. 1 g of Si was sprayed on a 25 cm×12.5 cm piece of polyurethane film. S5 was allowed to dry 5 for minutes at room temperature. The gel on the embossed polyethylene film was laminated with the primed polyurethane film and cured for 3 minutes at 80° C.

C10—Coat 250 g/m² gel precursor on an embossed polyethylene film. The gel precursor was cured for 20 min at 80° C. 1 g of S6 was sprayed on a 25 cm×12.5 cm piece of polyurethane film. Si was allowed to dry 5 for minutes at room temperature. The gel on the embossed polyethylene film was laminated with the primed polyurethane film and cured for 3 minutes at 80° C.

C11—Coat 250 g/m² gel precursor on an embossed polyethylene film. The gel precursor was cured for 20 min at 80° C. 1 g of S7 was sprayed on a 25 cm×12.5 cm piece of polyurethane film. S1 was allowed to dry 5 for minutes at room temperature. The gel on the embossed polyethylene film was laminated with the primed polyurethane film and cured for 3 minutes at 80° C.

C12—Coat 250 g/m² gel precursor on an embossed polyethylene film. The gel precursor was cured for 20 min at 80° C. 1 g of S8 was sprayed on a 25 cm×12.5 cm piece of polyurethane film. S1 was allowed to dry 5 for minutes at room temperature. The gel on the embossed polyethylene film was laminated with the primed polyurethane film and cured for 3 minutes at 80° C.

C13—Coat 250 g/m² gel precursor on an embossed polyethylene film. The gel precursor was cured for 6 min at 140° C. The gel on the embossed polyethylene film was laminated with a 25 cm×12.5 cm piece of polyurethane film and cured for 3 minutes at 140° C.

C14—Coat 250 g/m² gel precursor mixed with 0.5% TNBT and 0.5% TMMS on an untreated polyurethane film. The gel on the polyurethane film was laminated with a piece of Mylar® and cured for 6 minutes at 140° C.

C15—A 25 cm×12.5 cm piece of polyurethane film was wiped with S9 and then coated with 250 g/m² gel precursor. The gel on the polyurethane film was laminated with a piece of Mylar® and cured for 6 minutes at 140° C.

B. C16—Coat 250 g/m² gel precursor on an embossed polyethylene film. The gel precursor was cured for 20 min at 80° C. The gel was then laminated with untreated polyurethane film and cured for 3 minutes at 80° C.

C. C17—Coat 250 g/m² gel precursor on an embossed polyethylene film. The gel precursor was cured for 20 min at 80° C. The gel was then laminated with a polyurethane film treated with S9 and cured for 3 minutes at 80° C.

D. Testing

The above compositions were tested with a peel test in which a 2.54 cm strip was peeled at 180° at a rate of 1 meter/minute speed at 22° C. The following Table provides the results.

E. Examples to Show the Increase in Adhesion to PU Provided by the Use of Titanate

| Trial | Construction | Peel Test Result | observation |
|---|---|---|---|
| 1 | C13 | 55.3 g/cm | Adhesive failure on PU side, leaving a clean PU surface and a non-damaged tacky gel. |
| 2 | C14 | 308.5 g/cm | Cohesive failure, material on both sides |
| 3 | C15 | 151.3 g/cm | Adhesive failure on PU side. |
| 4 | C1 | 111.1 g/cm | Cohesive failure, material on both sides |
| 5 | C2 | 183.8 g/cm | Cohesive failure, material on both sides |
| 6 | C3 | 184.6 g/cm | Cohesive failure, material on both sides |
| 7 | C4 | 167.4 g/cm | Cohesive failure, material on both sides |

Examples to Show the Transfer Process from PE Film to PU Film

| Trial | Construction | Peel Test Result | observation |
|---|---|---|---|
| 8 | C16 | 23.2 g/cm | Total adhesive failure on PU side, leaving a clean PU surface and a non-damaged tacky gel |
| 9 | C17 | 43.6 g/cm | Transfer to PU: total adhesive failure on PE side, leaving a clean PE surface and a non-damaged tacky gel |
| 10 | C5 | 40.2 g/cm | Transfer to PU: total adhesive failure on PE side, leaving a clean PE surface and a non-damaged tacky gel |
| 11 | C6 | 43.5 g/cm | Transfer to PU: total adhesive failure on PE side, leaving a clean PE surface and a non-damaged tacky gel |
| 12 | C7 | 43.6 g/cm | Transfer to PU: total adhesive failure on PE side, leaving a clean PE surface and a non-damaged tacky gel |
| 13 | C8 | 36.2 g/cm | Transfer to PU: total adhesive failure on PE side, leaving a clean PE surface and a non-damaged tacky gel |

-continued

| Trial | Construction | Peel Test Result | observation |
|---|---|---|---|
| 14 | C9 | 41.3 g/cm | Transfer to PU: total adhesive failure on PE side, leaving a clean PE surface and a non-damaged tacky gel |
| 15 | C10 | 38.0 g/cm | Transfer to PU: total adhesive failure on PE side, leaving a clean PE surface and a non-damaged tacky gel |
| 16 | C11 | 38.1 g/cm | Transfer to PU: total adhesive failure on PE side, leaving a clean PE surface and a non-damaged tacky gel |
| 17 | C12 | 41.5 g/cm | Transfer to PU: total adhesive failure on PE side, leaving a clean PE surface and a non-damaged tacky gel |

The claimed invention is:

1. A method for adhering a silicone gel to a substrate comprising:
forming a layer of a silicone gel on a releasable substrate;
treating a surface of the silicone gel with a primer selected from titanate materials, zirconate materials, Si—H containing siloxanes and platinum materials;
applying the treated surface of the silicone gel to a first substrate; removing the releasable substrate from the silicone gel; and
applying the silicone gel to a surface of a second substrate to which the silicone gel is to be adhered.

2. The method according to claim 1 in which the first substrate is a plastic selected from the group consisting of polyolefins, polyvinyls, polyurethanes and polyurethane-ureas, polyvinyl chloride derivatives, polyacrylic and polyacrylates derivatives, polyacrylonitrile, polyesters, cellulosic films, polyimides, polyamides, epoxy and phenolic plastics, polycarbonates, phenoplastes, epoxy resins, fluorinated polymers, polyoxymethylenes, polyphenylene oxides, polysulfones, polyphenyl sulfide, silicones and polysaccharide based materials.

3. The method according to claim 1 in which the first substrate is selected from the group consisting of natural macromolecular materials, collagen, wood, cork, leather, metals, glass, ceramics or composite.

4. The method according to claim 1 in which the layer of silicone gel has a thickness in the range of about 0.1 mm to 5 mm.

5. The method according to claim 2 in which the plastic is in the form of a prosthesis.

6. The method according to claim 1 wherein the gel has a tack in the range of 50 g to 500 g when measured by a probe tack tester.

7. The method according to claim 1 wherein the primer is diluted in a diluent selected from volatile silicones, hydrocarbons and alcohols.

8. The method according to claim 1 wherein the primer is applied by spraying, brushing, coating with a blade, roll transfer coating, wiping or dipping.

9. The method as set forth in claim 1 wherein the silicone gel is cured prior to the step of treating the surface of the silicone gel with the primer.

10. The method as set forth in claim 9 wherein the primer comprises tetra-n-butyl titanate (TNBT).

11. The method as set forth in claim 10 wherein the primer further comprises trimethoxymethylsilane (TMMS).

12. The method as set forth in claim 7 wherein the diluent is 2-propanol (IPA), hexamethyldisiloxane (HMDS), or a mixture thereof.

13. A method for adhering a silicone gel to a substrate comprising:
forming a layer of a silicone gel on a releasable substrate;
treating a surface of a first substrate with a primer selected from titanate materials, zirconate materials, Si—H containing siloxanes and platinum materials;
joining the treated surface of the first substrate with the silicone gel;
removing the releasable substrate from the silicone gel; and
applying the silicone gel to a surface of a second substrate to which the silicone gel is to be adhered.

14. The method according to claim 13 in which the first substrate is a plastic selected from the group consisting of polyolefins, polyvinyls, polyurethanes and polyurethane-ureas, polyvinyl chloride derivatives, polyacrylic and polyacrylates derivatives, polyacrylonitrile, polyesters, cellulosic films, polyimides, polyamides, epoxy and phenolic plastics, polycarbonates, phenoplastes, epoxy resins, fluorinated polymers, polyoxymethylenes, polyphenylene oxides, polysulfones, polyphenyl sulfide, silicones and polysaccharide based materials.

15. The method according to claim 13 in which the first substrate is selected from the group consisting of natural macromolecular materials, collagen, wood, cork, leather, metals, glass, ceramics or composite.

16. The method according to claim 13 in which the layer of silicone gel has a thickness in the range of about 0.1 mm to 5 mm.

17. The method according to claim 14 in which the plastic is in the form of a prosthesis.

18. The method according to claim 13 wherein the gel has a tack in the range of 50 g to 500 g when measured by a probe tack tester.

19. The method according to claim 13 wherein the primer is diluted in a diluent selected from volatile silicones, hydrocarbons and alcohols.

20. The method according to claim 13 wherein the primer is applied by spraying, brushing, coating with a blade, roll transfer coating, wiping or dipping.

21. The method as set forth in claim 13 wherein the silicone gel is cured prior to the step of joining the treated surface of the first substrate with the silicone gel.

22. The method as set forth in claim 21 wherein the primer comprises tetra-n-butyl titanate (TNBT).

23. The method as set forth in claim 22 wherein the primer further comprises trimethoxymethylsilane (TMMS).

24. The method as set forth in claim 19 wherein the diluent is 2-propanol (IPA), hexamethyldisiloxane (HMDS), or a mixture thereof.

* * * * *